US 11,696,754 B2

(12) United States Patent
Cichocki, Jr.

(10) Patent No.: US 11,696,754 B2
(45) Date of Patent: Jul. 11, 2023

(54) METHODS OF MAKING SUTURE NEEDLES WITH LOCALIZED REGIONS FOR BENDING

(71) Applicant: Ethicon, Inc., Somerville, NJ (US)

(72) Inventor: Frank Richard Cichocki, Jr., Easton, PA (US)

(73) Assignee: Ethicon, Inc., Raritan, NJ (US)

( * ) Notice: Subject to any disclaimer, the term of this patent is extended or adjusted under 35 U.S.C. 154(b) by 687 days.

(21) Appl. No.: 16/282,652

(22) Filed: Feb. 22, 2019

(65) Prior Publication Data
US 2020/0268379 A1 Aug. 27, 2020

(51) Int. Cl.
| | |
|---|---|
| *A61B 17/062* | (2006.01) |
| *A61B 17/06* | (2006.01) |
| *A61B 17/04* | (2006.01) |
| A61B 17/34 | (2006.01) |
| A61B 17/00 | (2006.01) |

(52) U.S. Cl.
CPC .... *A61B 17/06066* (2013.01); *A61B 17/0482* (2013.01); *A61B 17/062* (2013.01); *A61B 17/3478* (2013.01); *A61B 2017/00862* (2013.01); *A61B 2017/0608* (2013.01); *A61B 2017/06095* (2013.01)

(58) Field of Classification Search
CPC .............................................. A61B 17/06066
See application file for complete search history.

(56) References Cited

U.S. PATENT DOCUMENTS

| | | | |
|---|---|---|---|
| 3,265,070 | A | 8/1966 | Kurtz |
| 4,327,655 | A | 5/1982 | Addy et al. |
| 4,981,149 | A | 1/1991 | Toon et al. |
| 5,041,127 | A | 8/1991 | Troutman |
| 5,219,358 | A | 6/1993 | Bendel et al. |
| 5,797,961 | A | 8/1998 | Smith et al. |
| 5,897,572 | A | 4/1999 | Schulsinger et al. |
| 5,935,138 | A | 8/1999 | McJames, II et al. |
| 6,322,581 | B1 | 11/2001 | Fakuda et al. |
| 7,727,257 | B2 | 6/2010 | Loubens et al. |
| 8,066,737 | B2 | 11/2011 | Meade et al. |
| 2004/0002724 | A1 | 1/2004 | Falahee |
| 2006/0047309 | A1 | 3/2006 | Cichocki |
| 2012/0010655 | A1 | 1/2012 | Lin |
| 2015/0027598 | A1* | 1/2015 | Seng ................... A61L 31/022 148/578 |

FOREIGN PATENT DOCUMENTS

| | | |
|---|---|---|
| CN | 201755238 | 3/2011 |
| CN | 201782788 | 4/2011 |
| CN | 204839615 | 12/2015 |
| CN | 204863323 | 12/2015 |
| CN | 206777363 | 12/2017 |
| WO | 2006065913 | 6/2006 |
| WO | WO-2012000638 A1 * | 1/2012 ............. C21D 6/004 |

OTHER PUBLICATIONS

International Search Report issued in corresponding International Application No. PCT/IB2020/051383, dated Jun. 2, 2020, 2 pages.

* cited by examiner

*Primary Examiner* — Jophy S. Koshy

(57) ABSTRACT

A method of making a suture needle having a bendable region includes obtaining a suture needle made of a martensitic alloy having an austenitic transition temperature. The suture needle has a proximal section, a distal section with a sharpened tip, and a bendable region located between the proximal and distal sections. The method includes heating the suture needle to a first temperature that is greater than the austenitic transition temperature of the martensitic alloy and quenching the suture needle to room temperature to harden the martensitic alloy, After heating and quenching, the bendable region of the suture needle is heated locally to a second temperature that is above 800 degrees Celsius, but below the austenitic transition temperature of the martensitic alloy so that the bendable region is softened and made more flexible relative to the proximal and distal sections of the suture needle.

16 Claims, 8 Drawing Sheets

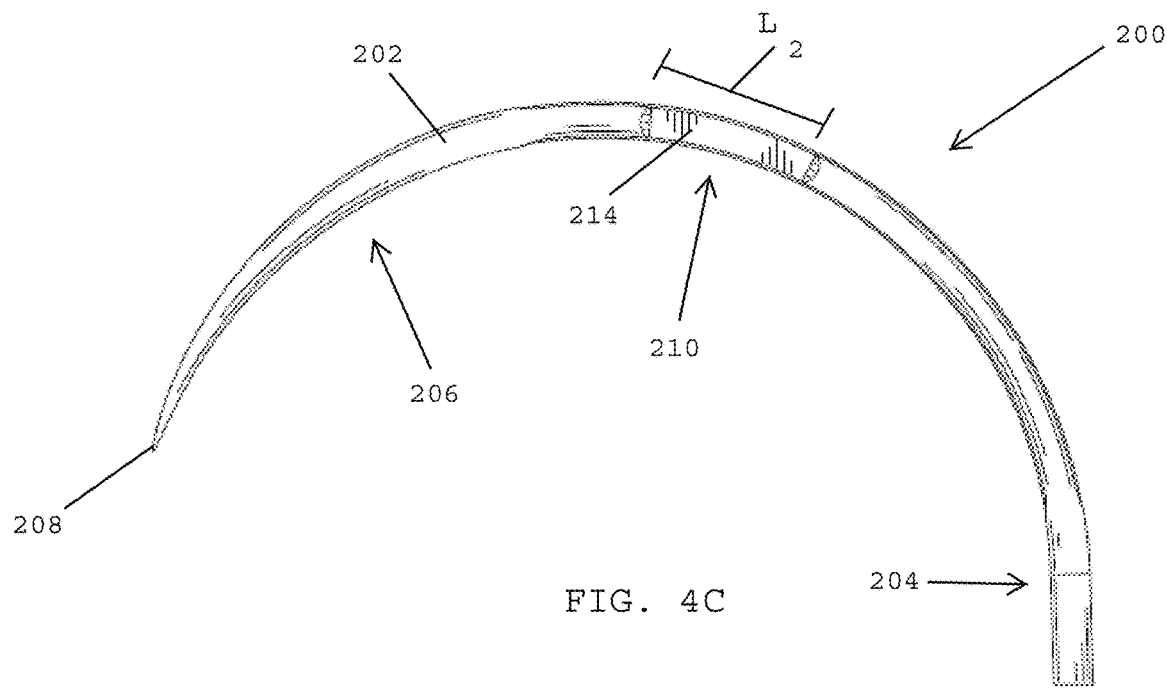
FIG. 4C
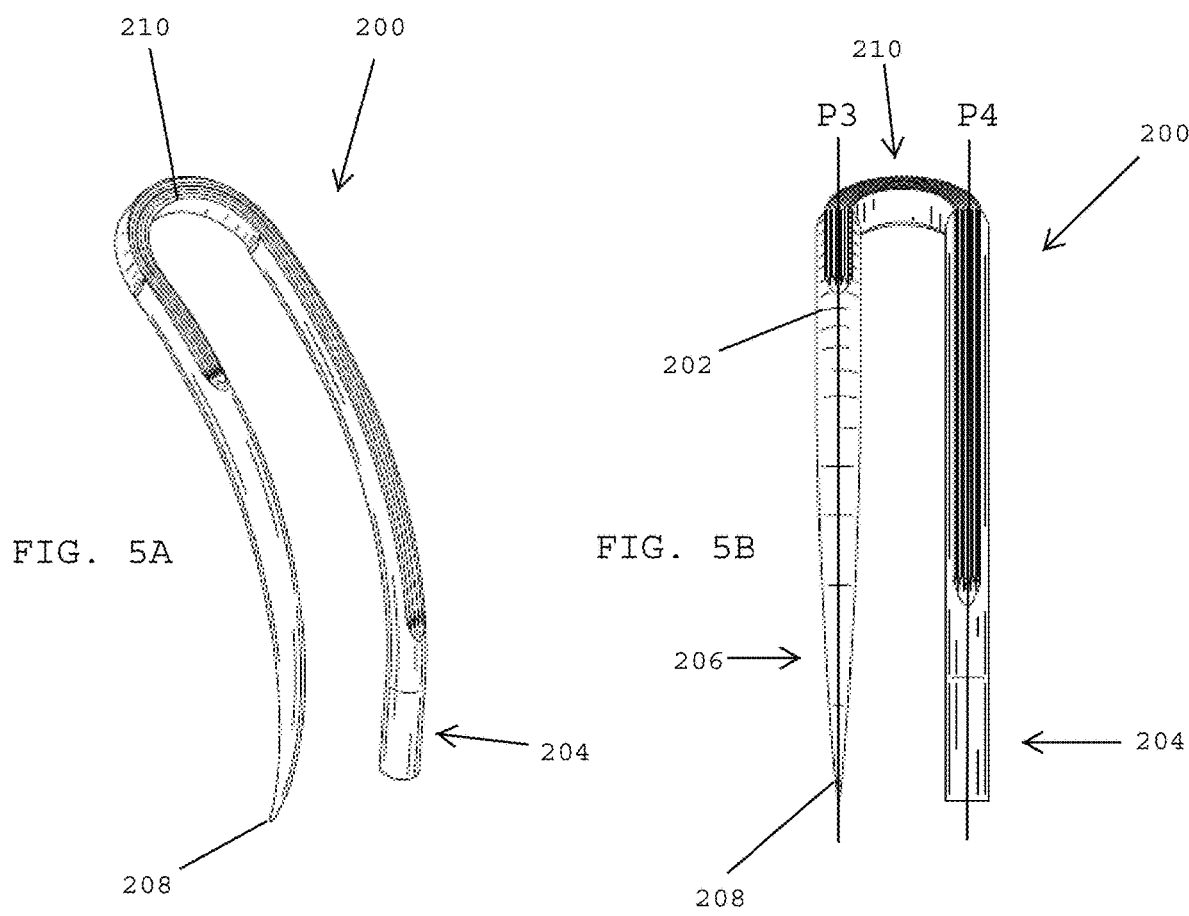
FIG. 5A
FIG. 5B

METHODS OF MAKING SUTURE NEEDLES WITH LOCALIZED REGIONS FOR BENDING

BACKGROUND OF THE INVENTION

Field of the Invention

The present patent application is generally related to medical devices used in surgical procedures, and is more specifically related to suture needles use for suturing tissue.

Description of the Related Art

In a conventional suture needle manufacturing process, wire is removed from a spool, straightened, and then cut into needle blanks. The needle blanks are then subjected to a variety of conventional forming, grinding and shaping processes to produce suture needles having distal piercing points and proximal suture mounting sections (e.g., drilled holes). The suture needles are typically tapered and may have cutting edges or a sharpened tip. Conventional suture needles are typically curved by bending the needle blanks, but may also have a straight configuration, or a configuration having a straight section and a curved section. In some instances, portions of suture needles have gripping surfaces to assist in grasping the needles with conventional needle holding instruments.

Suture needles are typically made from stainless steels. The different types of stainless steels that are used include martensitic stainless steel (420SS), austenitic stainless steel (302SS), and martensitic-aged (mar-aged) stainless steel (455SS).

Martensitic stainless steels (420SS) can be high-carbon or low-carbon steels built around the Type 420 composition of iron, 12% chromium, and up to 0.4% carbon. Martensitic stainless steel is hardenable by heat treatment (e.g., by quenching, or by quenching and tempering). The alloy composition and the high cooling rate of quenching enable the formation of martensite. Tempered martensite provides steel with good hardness and high toughness. It is often used for making medical devices and tools such as scalpels, razors and suture needles. See "Martensitic stainless steel" at www.wikipedia.org.

Austenitic stainless steels (302SS) possess austenite as their primary crystalline structure. The austenite crystalline structure is achieved by sufficient additions of the austenite stabilizing elements nickel, manganese and nitrogen. Due to their crystalline structure austenitic steels are not hardenable by heat treatment. See "Austenitic stainless steel" at www.wikipedia.org.

Martensitic-aged (mar-aged) stainless steels (455SS) are steels that are known for possessing superior strength and toughness without losing malleability. The "aging" portion of the word Mar-aged refers to the extended heat-treatment process. These steels are a special class of low-carbon, ultra-high-strength steels that derive their strength not from carbon, but from a combination of work hardening and precipitation of intermetallic compounds. The principal alloying element is 8 to 25 wt. % nickel. Secondary alloying elements, which include cobalt, molybdenum and titanium, are added to produce intermetallic precipitates. See "Maraging steel" at www.wikipedia.org.

Surgeons typically use trocars to position suture needles at surgical sites. The size of a suture needle that can be passed through the trocar to a surgical site is limited by the size of the opening in the trocar. In many instances, surgeons desire to use larger needles for closing surgical wounds and repairing anatomical features, however, passing the larger needles through smaller trocars is difficult. For example, 5 mm trocars are often used during minimally invasive surgeries (MIS), however, surgeons cannot pass the larger suture needles through the 5 mm trocars so they are forced to use only smaller suture needles.

The smaller suture needles are less than optimal because, inter alia, they often require a surgeon to make many more passes of the needle and suture through tissue, which lengthens the surgical procedure and can frustrate the surgeon. Using smaller needles may also produce a bite distance that puts the wound or anatomical feature at risk of dehiscence.

In addition, larger-sized sutures cannot be easily attached to the smaller suture needles. Thus, when fine sutures are passed through tissue with a smaller bite size, a cheese wire effect may result, whereby the suture cuts through the tissue it is intended to hold.

Thus, there is a need for improved suture needles that may be passed through relatively smaller trocars (e.g., 5mm trocars) that are used in surgical procedures. There is also a need for systems, devices and methods for passing larger suture needles through the relatively smaller torcars. Moreover, there remains a need for improved systems and methods of manufacturing surgical needles, such as those made of martensitic, austenitic, and martensitic-aged stainless steels, that have at least one bendable region, while the remainder of the needle exhibits the exceptional strength, stiffness and hardness expected of a typical suture needle.

SUMMARY OF THE INVENTION

In one embodiment, a method of making a suture needle having a bendable region preferably includes obtaining a suture needle made of a martensitic alloy having an austenitic transition temperature.

In one embodiment, the suture needle made of the martensitic alloy may have a proximal section, a distal section with a sharpened tip, and a bendable region located between the proximal and distal sections. The proximal section may have a suture attachment hole formed therein, such as at a proximal-most end of the proximal section.

In one embodiment, a method of making a suture needle having a bendable region desirably includes heating the suture needle to a first temperature that is greater than the austenitic transition temperature of the martensitic alloy and quenching the suture needle to room temperature to harden the martensitic alloy.

In one embodiment, the first temperature that is above the austenitic transition temperature of the martensitic alloy may be between about 950-1,040 degrees Celsius.

In one embodiment, the quenching step preferably includes using a gas or a liquid for cooling the suture needle. In one embodiment, the cooling of the suture needle to room temperature desirably includes rapidly cooling the suture needle at a cooling rate that is greater than 100 degrees Celsius per minute.

The above-described heating and quenching steps preferably strengthen, stiffen, and/or harden the suture needle.

In one embodiment, after the heating and quenching steps, a method of making a suture needle having a bendable region preferably includes locally heating the bendable region of the suture needle to a second temperature that is above 800 degrees Celsius, but below the austenitic transition temperature of the martensitic alloy so that the bendable region is softened and made more flexible relative to the proximal and distal sections of the suture needle, which preferably remain stronger, stiffer, and/or hardened as described above.

In one embodiment, the second temperature for locally heating the bendable region of the suture needle may be between about 800-920 degrees Celsius.

In one embodiment, locally heating the bendable region may be accomplished by a variety of well known heating methodologies including but not limited to electrical resistance heating, laser heating, induction heating, flame heating, hot gas heating, and/or combinations thereof.

In one embodiment, the suture needle may be formed and/or shaped into a suture needle having a seagull shaped configuration in which the proximal section of the suture needle defines a proximal arc, the distal section of the suture needle defines a distal arc, and the bendable region of the suture needle defines a V-shaped or U-shaped section that interconnects inner ends of the proximal and distal arcs. In one embodiment, the proximal arc, the distal arc, and the V-shaped or U-shaped section of the seagull shaped suture needle lie in a common plane.

In one embodiment, the suture needle may be formed and/or shaped into a suture needle having a folded configuration in which the suture needle is folded in half so that the proximal section of the suture needle lies in a first plane, the distal section of the suture needle lies in a second plane that is different than the first plane, and the bendable region of the suture needle interconnects inner ends of the proximal and distal sections of the suture needle. In one embodiment, when the suture needle is in the folded configuration, the sharpened tip of the distal section of the suture needle is desirably adjacent a proximal-most end of the proximal section of the suture needle.

In one embodiment, after hardening the proximal and distal ends of the suture needle and softening the bendable region of the suture needle, the suture needle may be tempered for improving and/or increasing the ductility of the suture needle, and particularly the proximal and distal sections of the suture needle that have been hardened. In one embodiment, the suture needle may be tempered by heating the suture needle to a temperature of about 150-430 degrees Celsius.

In one embodiment, the suture needle may be shaped by curving the suture needle along its length, e.g., making a semi-circular or half-circle suture needle, making a folded suture needle, making a seagull shaped suture needle. In one embodiment, a suture needle may have one or more curves formed along the length of the suture needle (e.g., the arc shape of the distal section).

In one embodiment, the proximal and distal sections of the suture needle body preferably define a first outer wire diameter (i.e., a first thickness), and the bendable region of the suture needle preferably defines a second outer wire diameter (i.e., a second thickness) that is smaller than the first outer wire diameter of the respective proximal and distal sections of the suture needle.

In one embodiment, the bendable region of a suture needle may include one or more flat surfaces. In one embodiment, the bendable region of the suture needle is desirably thinner than the proximal and distal sections of the suture needle, which enhances the flexibility of the bendable region relative to the more rigid proximal and distal sections of the suture needle.

In one embodiment, a method of making a suture needle having a bendable region preferably includes obtaining a wire made of a martensitic alloy have an austenitic transition temperature, heating the wire to a first temperature that is greater than 800 degrees Celsius and less than the austenitic transition temperature to soften the wire, and after the heating step, cooling the wire to room temperature. In one embodiment, the first temperature may be between about 800-920 degrees Celsius.

In one embodiment, after the cooling step, a method preferably includes using a section of the cooled wire for forming a suture needle having a proximal section, a distal section with a sharpened tip, and a bendable region located between the proximal and distal sections.

In one embodiment, after the suture needle has been formed, a method of making a suture needle having a bendable region desirably includes locally heating the proximal and distal sections of the suture needle to a second temperature that is above the austenitic transition temperature of the martensitic alloy for hardening the proximal and distal sections of the suture needle while maintaining the bendable region of the suture needle at a third temperature that is below the austenitic transition temperature of the martensitic alloy so that the bendable region is softer and more flexible than the stronger, stiffer and/or harder proximal and distal sections of the suture needle. In one embodiment, the second temperature may be about 950-1,040 degrees Celsius.

In one embodiment, the locally heating step may include various heating methodologies including but not limited to electrical resistance heating, laser heating, induction heating, and flame heating.

In one embodiment, after locally heating the proximal and distal sections of the suture needle, the method may include quenching (e.g., rapidly cooling) the suture needle to room temperature for preferably hardening the proximal and distal sections of the suture needle.

In one embodiment, after quenching the suture needle, the suture needle may be tempered for increasing the ductility of the suture needle.

In one embodiment, the suture needles may be formed and/or shaped into a seagull shaped configuration or a folded configuration (e.g., folded in half). In one embodiment, a suture needle having a bendable region may be straight.

In one embodiment, the proximal and distal sections of the suture needle preferably define a first outer wire diameter and the bendable region of the suture needle preferably defines a second outer wire diameter that is smaller than the first outer wire diameter of the respective proximal and distal sections. In one embodiment, the bendable region is preferably thinner than the proximal and distal sections of the suture needle for making the bendable region more flexible than the proximal and distal sections.

In one embodiment, a method of making a suture needle having a bendable region desirably includes drawing a wire made of an austenitic alloy or a martensitic-aged (mar-aged) alloy to obtain a wire strand. The wire strand may be hardened as it is drawn.

In one embodiment, a method may include heating the wire strand to a first temperature of between about 450-700 degrees Celsius to harden the wire strand made of the martensitic-aged (mar-aged) alloy.

In one embodiment, a method of making a suture needle having a bendable region desirably includes using a section of the hardened wire strand for forming a suture needle having a proximal section, a distal section with a sharpened tip, and the bendable region located between the proximal and distal sections.

In one embodiment, a method includes locally heating the bendable region of the suture needle to a second temperature that is greater than 700 degrees Celsius while maintaining the proximal and distal sections of the suture needle at a third temperature that is below 700 degrees Celsius so that the bendable region of the suture needle is softer and more flexible than the proximal and distal sections of the suture needle.

In one embodiment, the locally heating step may include various heating methodologies including but not limited to electrical resistance heating, laser heating, induction heating, flame heating, and/or hot gas heating.

In one embodiment, the wire strand is a martensitic-aged alloy, and heating the wire strand to the first temperature desirably includes precipitation heat treating the wire strand.

In one embodiment, the proximal and distal sections of the suture needle preferably define a first outer wire diameter and the bendable region of the suture needle preferably defines a second outer wire diameter that is smaller than the first outer wire diameter of the respective proximal and distal sections of the suture needle.

In one embodiment, a method of making a suture needle having a bendable region preferably includes obtaining a wire made of a martensitic-aged (mar-aged) alloy, using a section of the wire for forming a suture needle having a proximal section, a distal section with a sharpened tip, and a bendable region located between the proximal and distal sections, and locally heating the bendable region of the suture needle to a first temperature that is greater than 700 degrees Celsius while maintaining the proximal and distal sections of the suture needle at a temperature that is below 700 degrees Celsius so that the bendable region of the suture needle is softer and more flexible than the proximal and distal sections of the suture needle.

In one embodiment, after the locally heating step, a method desirably includes cooling the suture needle to room temperature, and, after the cooling step, heating the proximal and distal sections of the suture needle to a second temperature of about 450-700 degrees Celsius while maintaining the bendable region of the suture needle below the second temperature.

In one embodiment, the martensitic-aged alloy may be 455SS or a stainless steel sold under the trademark ETHAL-LOY having a composition of about 73% iron, 12% chrome, 10% nickel 10%, 3% molybdenum 3%, and 2% titanium.

In one embodiment, the locally heating step may include electrical resistance heating, laser heating, induction heating, flame heating, hot gas heating, and combinations thereof.

In one embodiment, a method may include clamping the bendable region of the suture needle with a heat sink while heating the proximal and distal sections of the suture needle to the second temperature, which preferably insulates the bendable region from the heat at the second temperature.

These and other preferred embodiments of the present patent application will be described in more detail below.

BRIEF DESCRIPTION OF THE DRAWINGS

FIG. 4C shows a side view of the suture needle shown in FIGS. 4A and 4B.

FIG. 5A shows a perspective view of the suture needle of FIGS. 4A-4C after it has been folded in half, in accordance with one embodiment of the present patent application.

FIG. 5B shows a distal end view of the folded in half suture needle shown in FIG. 5A.

DETAILED DESCRIPTION OF PREFERRED EMBODIMENTS

Figure 1A:
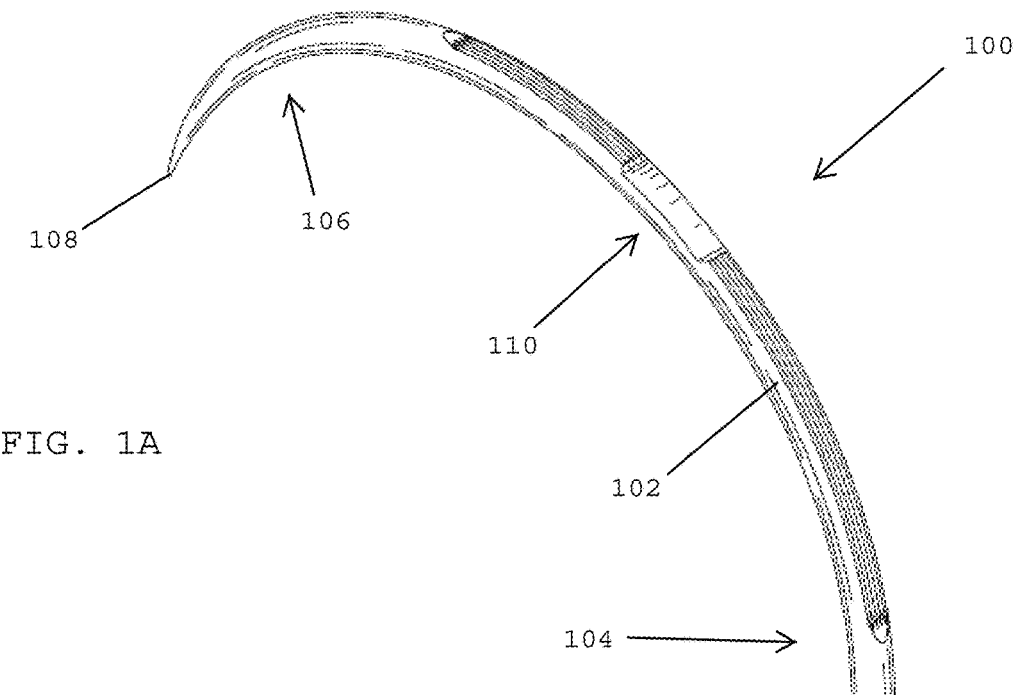
FIG. 1A shows a perspective view of a suture needle having a bendable region, in accordance with one embodiment of the present patent application.
Figure 1B:
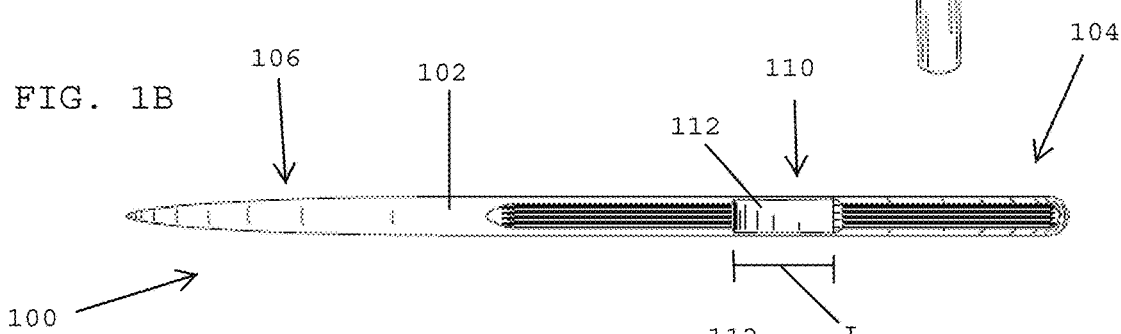
FIG. 1B shows a top plan view of the suture needle shown in FIG. 1A.
Figure 1C:
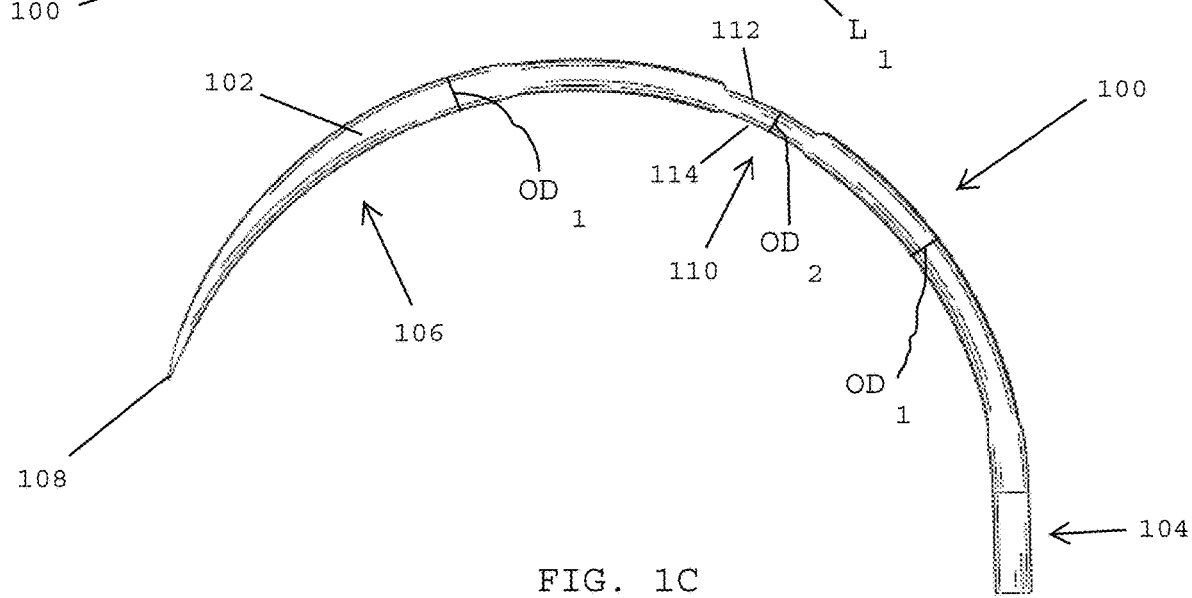
FIG. 1C shows a side view of the suture needle shown in FIGS. 1A and 1B.

Referring to FIGS. 1A-1C, in one embodiment, a method of making a suture needle having a bendable region preferably includes obtaining a needle blank and shaping the needle blank to form a suture needle 100 having an elongated body 102 with a proximal section 104 and a distal section 106 with a sharpened tip 108. In one embodiment, the suture needle 100 preferably includes a bendable region 110 that is located between the proximal and distal sections 104, 106 thereof. In one embodiment, the bendable region 110 is preferably positioned along the length of the suture needle, between the proximal and distal sections thereof. In one embodiment, the bendable region 110 is preferably more bendable and/or flexible than other regions of the needle, and particularly the proximal and distal sections of the needle.

In one embodiment, the bendable region may be midway between proximal and distal ends of the suture needle. In one embodiment, the bendable region may be closer to the distal end than the proximal end of the suture needle. In one embodiment, the bendable region may be closer to the proximal end than the distal end of the suture needle.

In one embodiment, the bendable region may be formed by reducing a cross-sectional wire diameter of the suture needle within the bendable so that the bendable region is thinner than the proximal and distal sections of the suture needle. In one embodiment, the bendable region may be formed by making the bendable region of a material that is softer and/or more flexible than the material that is used to make the proximal and distal sections of the needle. In one embodiment, the bendable region may be treated with heat to soften the material within the bendable region to make it more flexible than the proximal and distal sections of the suture needle.

In one embodiment, the bendable region 110 may include a first flat surface 112 located on a top side of the elongated body 102 of the suture needle 100 and a second flat surface 114 located on an underside of the elongated body 102 of the suture needle 100.

In one embodiment, the bendable region 110 preferably has a smaller outer wire diameter than the outer wire diameter of the proximal and distal sections 104, 106 of the suture needle 100, which are located on opposite sides of the bendable region 110. In one embodiment, the proximal and distal sections 104, 106 of the elongated body 102 preferably have respective outer wire diameters $OD_1$ that are greater than the outer wire diameter $OD_2$ of the bendable region 110, which is defined by the first and second flat surfaces 112, 114.

In one embodiment, the proximal and distal sections 104, 106 of the elongated body 102 of the suture needle 100 preferably define a first outer wire diameter and the bendable region 110 of the suture needle 100 defines a second outer wire diameter that is smaller than the first outer wire diameter of the respective proximal and distal sections. In one embodiment, the bendable region 110 of the suture needle 100 preferably includes one or more flat surfaces, whereby the bendable region 110 of the suture needle 100 is thinner than the proximal and distal sections 104, 106 of the suture needle 100.

In one embodiment, the bendable region 110 has a length $L_1$ (FIG. 1B) that is preferably equal to or greater than the outer wire diameters $OD_1$ of the proximal and distal sections 104, 106 of the elongated body 102 of the suture needle 100.

Figure 2A:
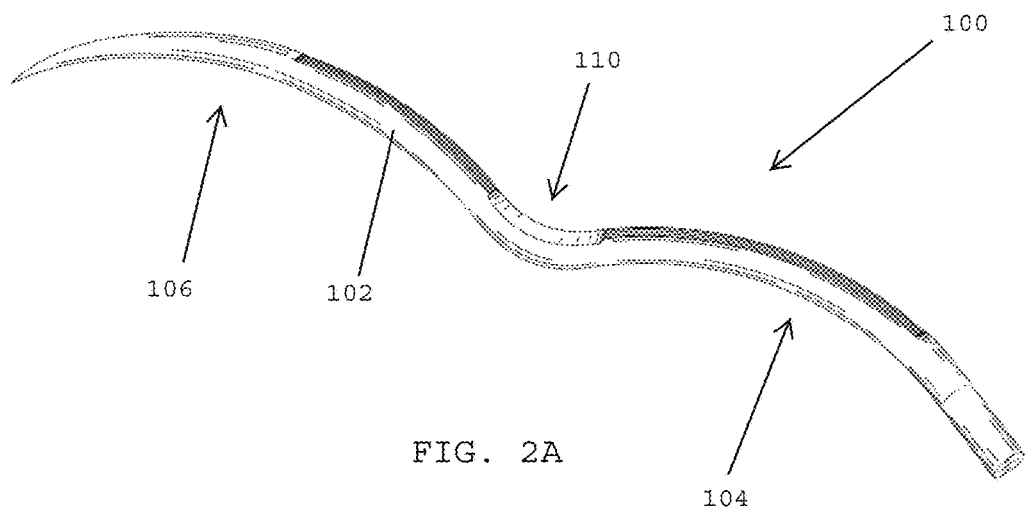
FIG. 2A shows a perspective view of the suture needle of FIGS. 1A-1C after it has been bent into a seagull shaped configuration, in accordance with one embodiment of the present patent application.
Figure 2B:
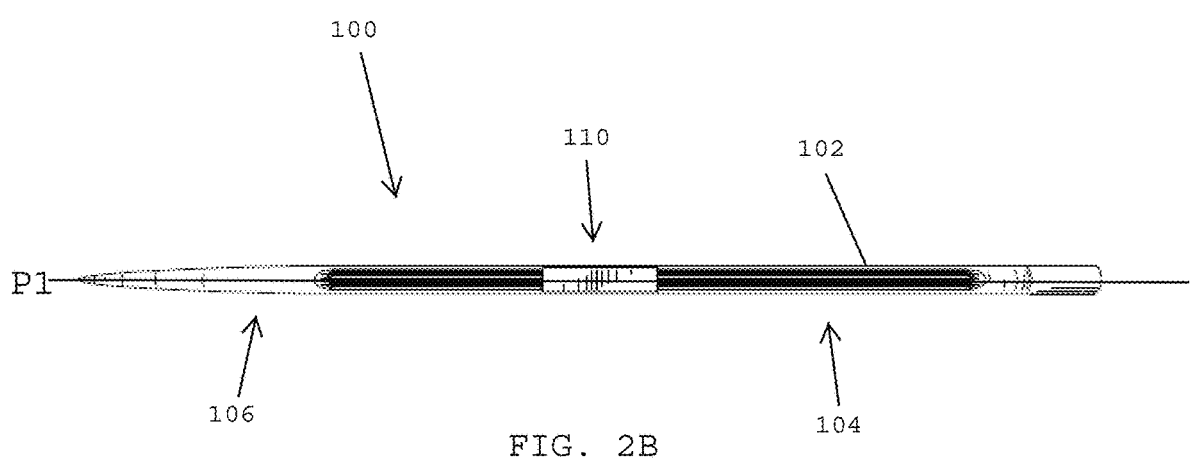
FIG. 2B shows a top plan view of the bent suture needle shown in FIG. 2A.
Figure 2C:
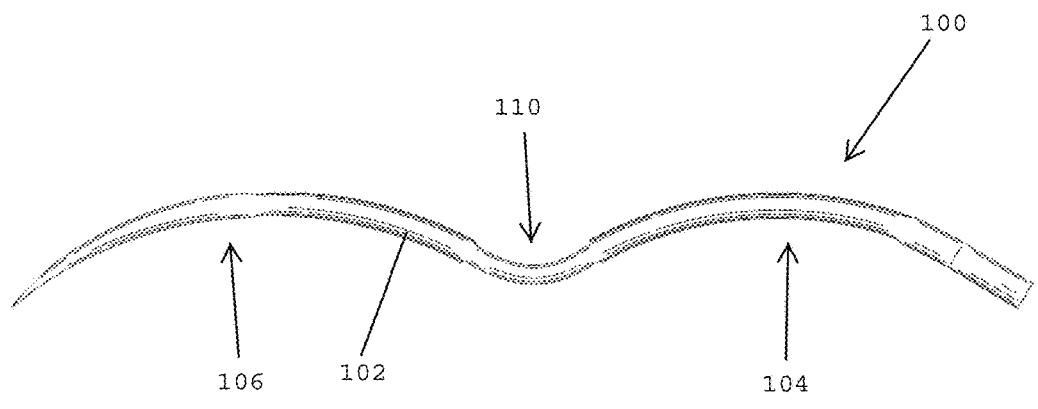
FIG. 2C shows a side view of the bent suture needle shown in FIGS. 2A and 2B.

Referring to FIGS. 2A-2C, in one embodiment, the bendable region 110 of the elongated body 102 of the suture needle 100 may be bent to provide a bent suture needle having a seagull shaped configuration. In one embodiment, the needle may be repeatedly transformed back and forth between the semi-circular or half-circle shaped configuration shown in FIGS. 1A-1C and the seagull shaped configuration shown in FIGS. 2A-2C. In one embodiment, as the suture needle 100 is bent into the seagull shaped configuration (FIG. 2C), the proximal section 104 and the distal section 106 of the needle, which are desirably more rigid than the bendable region 110, maintain their respective arc-shaped, curved, and/or semi-circular shaped configurations.

In one embodiment, when the elongated body 102 of the suture needle 100 has been bent into the seagull shape configuration of FIGS. 2A-2C, the proximal section 104 of the elongated body 102 preferably defines a proximal arc, the distal section 106 of the elongated body 102 preferably defines a distal arc, and the bendable region 110 of the elongated body 102 preferably defines a V-shaped or a U-shaped section that interconnects inner ends of the proximal and distal arcs of the respective proximal and distal sections 104, 106 of the elongated body 102 of the suture needle 100. In the seagull shaped configuration, the proximal arc, the distal arc, and the V-shaped or U-shaped section preferably lie in a common plane P1 (FIG. 2B).

Providing a suture needle 100 with a bendable region (i.e., a region that is more flexible or bendable than adjacent sections of the needle) preferably enables surgical personnel to reduce the overall height and/or dimension of the suture needle so that it may be passed through smaller trocars, such as those that are typically used in minimally invasive surgeries (MIS)(e.g., 5 mm trocars).

In one embodiment, a suture needle may have a bendable region for bending or folding the needle to reduce its outer dimension or profile for passing the suture needle through a trocar as disclosed in commonly assigned U.S. patent application Ser. No. 16/282.604, published as US 2020/0268378, now U.S. Pat. No. 11,311.288, the disclosure of which is hereby incorporated by reference herein. In one embodiment, a suture needle may have a thinner section, such as by forming flattened surfaces one or more outer surfaces of an elongated body of the suture needle, In one embodiment, the suture needle may be heat treated to produce a suture needle that is relatively more bendable in one or more locations, while the remainder of the needle is made to exhibit the exceptional strength, stiffness, and hardness expected of a typical suture needle (e.g., a stainless steel needle). In one embodiment, the bendable region of a suture needle may include a composition of a superelastic material (e.g., Nitinol), while the remainder of the suture needle is made of a material (e.g., stainless steel) that is relatively stronger, stiffer, and harder than the superelastic material found in the bendable region.

In one embodiment, a preferred method of making a suture needle with a bendable region may differ depending upon the particular type of alloy that is used for making the suture needle.

In one embodiment, suture needles having bendable regions that are made of martensitic alloys are processed differently from martensitic-aged and austenitic stainless steel alloys commonly used in needle manufacturing. For example, martensitic alloys may contain carbon and/or nitrogen, such as 420 stainless steel, which hardens when cooled rapidly. As a result, needles made of martensitic alloys may be processed differently from needles made of martensitic-aged (mar-aged) or austenitic stainless steel alloys.

In one embodiment, a method of making a suture needle having a bendable region, such as the suture needle shown and described in FIGS. 1A-1C and 2A-2C, preferably includes obtaining a suture needle made of a martensitic alloy having an austenitic transition temperature.

In one embodiment, the suture needle made of the martensitic alloy is heated to a first temperature that is greater than the austenitic transition temperature of the martensitic alloy. In one embodiment, the first temperature that is above the austenitic transition temperature is preferably between about 950-1,040 degrees Celsius.

In one embodiment, after heating the suture needle to the first temperature that is above the austenitic transition temperature, the suture needle is preferably quenched to room temperature to harden the martensitic alloy. In one embodiment, the quenching step may be accomplished by using a gas or a liquid for cooling the suture needle to room temperature. In one embodiment, cooling the suture needle to room temperature may include rapidly cooling the suture needle at a cooling rate that is greater than 100 degrees Celsius per minute.

In one embodiment, after the heating and quenching steps described above for hardening the suture needle, the bendable region of the suture needle is preferably heated to a second temperature that is above 800 degrees Celsius but below the austenitic transition temperature of the martensitic alloy so that the bendable region is softened and made more flexible relative to the proximal and distal sections of the suture needle that remain hardened from the initial heating and quenching steps described above.

In one embodiment, the second temperature used for locally heating the bendable region is preferably between about 800-920 degrees Celsius. In one embodiment, locally heating the bendable region may be accomplished using various heating methodologies including electrical resistance heating, laser heating, induction heating, flame heating, hot gas heating, and/or one or more combinations thereof.

In one embodiment, the suture needle may be formed and/or shaped into a suture needle having a seagull shaped configuration in which the proximal section of the suture needle defines a proximal arc, the distal section of the suture needle defines a distal arc, and the bendable region of the suture needle defines a V-shaped or U-shaped section that interconnects inner ends of the proximal and distal arcs of the respective proximal and distal sections of the suture needle. In one embodiment, the proximal arc, the distal arc, and the V-shaped or U-shaped section desirably lie in a common plane.

In one embodiment, the above-described heating, quenching, and locally heating steps for making the bendable region of the suture needle softer and more flexible and the proximal and distal sections of the suture needle relatively stronger, stiffer and harder than the bendable region may be performed before the suture needle is formed into the seagull shaped configuration, while the suture needle is being formed into the seagull shaped configuration, or after the suture needle has been formed into the seagull shaped configuration.

In one embodiment, the suture needle may be formed and/or shaped into a suture needle having a folded configuration in which the proximal section of the suture needle lies in a first plane, the distal section of the suture needle lies in a second plane that is different than the first plane, and the bendable region of the suture needle interconnects inner ends of the proximal and distal sections of the suture needle, whereby the sharpened tip of the distal section of the suture needle is adjacent a proximal-most end of the proximal section of the suture needle.

In one embodiment, the above-described heating, quenching, and locally heating steps for making the bendable region of the suture needle softer and more flexible and the proximal and distal sections of the suture needle relatively stronger, stiffer and harder may be performed before the suture needle is formed into the folded configuration, while the suture needle is being formed into the folded configuration, or after the suture needle has been formed into the folded configuration.

In one embodiment, the suture needles may be shaped into the seagull shaped configuration, the folded configuration, or any other bendable shaped configuration using one or more curving mandrels or one or more bending presses (e.g., using a tooling similar to three point bending fixtures commonly used to bend test beams). Combinations of bending presses and curving mandrels may also be used for shaping the suture needles.

While the transformation resulting from the heat treatment increases the mechanical strength of the martensitic suture needle, it is accomplished with an accompanying decrease in ductility. In order to improve the ductility of heat treated suture needle, the martensitic suture needle may be subsequently tempered.

The methods and processes that are used for heat treating suture needles may be varied. In one embodiment, the heat treatment may be performed using a continuous belt furnace whereby the suture needles are fed through a hot zone at the reaction temperature. In this process, the temperature of the suture needles preferably increases to the reaction temperature in a hot zone. The suture needles are then passed into a cooler zone where the transformation takes place. This process may take place under a protective atmosphere of nitrogen, hydrogen or an inert gas.

The suture needles may also be batch processed in a furnace. This process may also take place in a protective atmosphere of nitrogen, hydrogen or an inert gas.

For both of the previously-mentioned processes, the suture needles are desirably tempered after the initial heat treatment step in a separate furnace at a lower temperature. The tempering process may be performed in air or under an atmosphere of nitrogen or inert gas.

In one embodiment, after the heating, quenching, and locally heating steps, the suture needle may be tempered for increasing the ductility of the suture needle. In one embodiment, the entire suture needle including the proximal and distal sections and the bendable region is tempered. In one embodiment, the proximal and distal sections of the suture needle are tempered and the bendable region is not tempered. In one embodiment, the suture needle may be tempered by heating the suture needle to a temperature of about 150-430 degrees Celsius.

Figure 3:
FIG. 3 shows a method of drawing a strand of wire from a wire spool, in accordance with one embodiment of the present patent application.

Referring to FIG. 3, in one embodiment, a wire strand 180 may be drawn from a wire spool 182. The wire strand 180 may be hardened as it is drawn from the wire spool 182. The wire strand 180 may be used for forming one or more needle blanks that, in turn, may be used to make one or more suture needles.

Figure 4A:
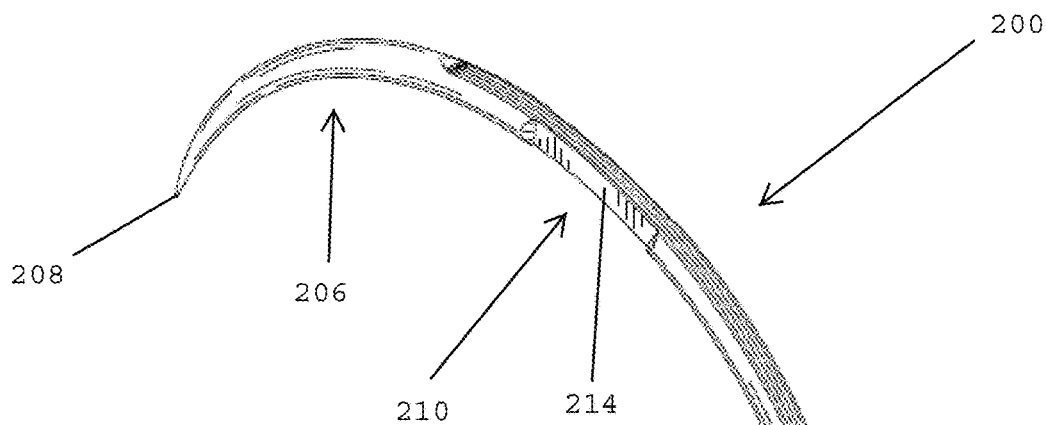
FIG. 4A shows a perspective view of a suture needle having a bendable region, in accordance with one embodiment of the present patent application.
Figure 4B:
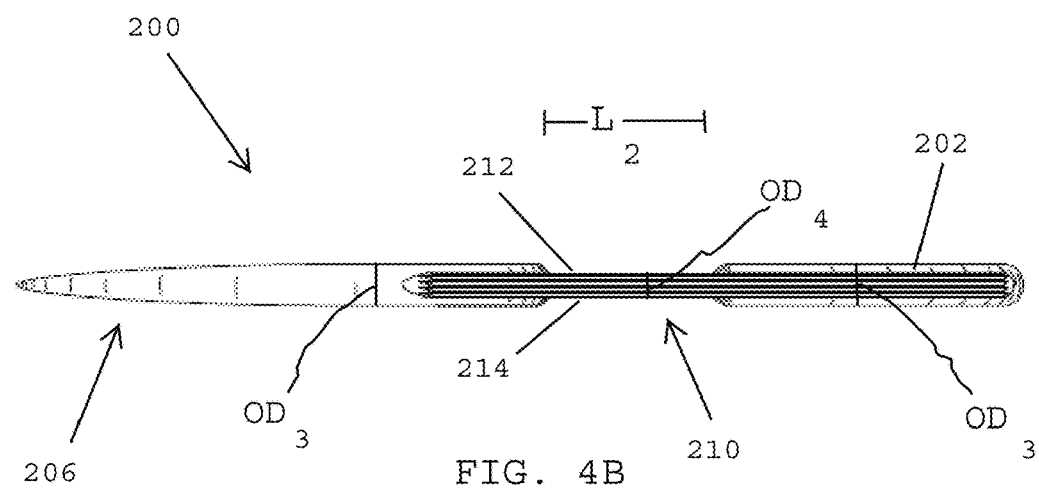
FIG. 4B shows a top plan view of the suture needle shown in FIG. 4A.

Referring to FIGS. 4A-4C, in one embodiment, a needle blank may be used to make a bendable suture needle 200 having an elongated body 202 with a proximal section 204, a distal section 206 with a sharpened tip 208, and a bendable region 210 that is located between the proximal and distal sections 204, 206 of the elongated body 202 of the suture needle 200.

In one embodiment, the bendable region 210 of the elongated body 202 is preferably defined by first and second flat surfaces 212, 214 (FIG. 4B) that are formed in the lateral sides of the elongated body 202. The flat surfaces 212, 214 preferably define a thinner section of the elongated body 202 that makes the bendable region 210 more flexible and/or bendable than the thicker proximal and distal sections 204, 206 of the elongated body 202 of the suture needle 200. Referring to FIG. 4B, in one embodiment, the proximal and distal sections 204, 206 of the elongated body 202 preferably define respective outer wire diameters $OD_3$ that are greater than the outer wire diameter $OD_4$ of the bendable region 210 of the elongated body 202.

In one embodiment, the length of the first and second flat surfaces 212, 214 that form the bendable region 210 of the suture needle 400 desirably define a length $L_2$ that is equal to or greater than the outer diameter $OD_3$ (FIG. 4B) of the respective proximal and distal sections 204, 206 of the elongated body 202 of the suture needle 200.

Referring to FIGS. 5A and 5B, in one embodiment, the suture needle 200 of FIGS. 4A-4C may be bent or folded at the bendable region 210, whereupon the sharpened tip 208 of the suture needle 200 is adjacent a proximal-most end of the proximal section 204 of the elongated body 202. In the bent or folded configuration shown in FIGS. 5A and 5B, the elongated body 202 of the suture needle 200 has a smaller height, dimension and/or profile than when the suture needle is an unbent, semi-circular configuration (e.g., the configuration shown in FIG. 4C).

Referring to FIG. 5B, in one embodiment, when the elongated body 202 has been bent into the folded configuration, the elongated body 202 is folded in half so that the proximal section 204 of the elongated body 202 preferably lies in a first plane P2 and the distal section 206 of the elongated body preferably lies in a second plane P3 that is different than the first plane P2. In one embodiment, the planes P2 and P3 are preferably parallel to one another. In the folded configuration, the bendable region 210 desirably interconnects inner ends of the respective proximal and distal sections 204, 206 of the elongated body 202. The proximal and distal sections 204, 206 preferable retain arc shapes as the suture needle is transformed between the unfolded configuration (FIGS. 4A-4C) and folded configuration (FIGS. 5A and 5B).

Referring to FIG. 3, in one embodiment, a method of making a suture needle having a bendable region desirably includes obtaining a wire 180 made of a martensitic alloy have an austenitic transition temperature, and heating the wire 180 to a first temperature that is greater than 800 degrees Celsius and less than the austenitic transition temperature to soften the wire. In one embodiment, the first temperature is preferably between about 800-920 degrees Celsius.

In one embodiment, after the heating step, the wire is preferably cooled to room temperature. Referring to FIGS. 4A-4C, in one embodiment, after cooling the wire to room temperature, a section of the cooled wire may be used for forming the suture needle 200 having the proximal section 204, the distal section 206 with the sharpened tip 208, and the bendable region 210 located between the proximal and distal sections.

In one embodiment, after forming the suture needle 200, the proximal and distal sections 204, 206 of the suture needle 200 may be locally heated to a second temperature that is above the austenitic transition temperature of the martensitic alloy for hardening the proximal and distal sections 204, 206 of the suture needle 200 while maintaining the bendable region 210 of the suture needle 200 at a temperature that is below the austenitic transition temperature of the martensitic alloy so that the bendable region 210 is softer and more flexible than the proximal and distal sections 204, 206 of the suture needle 200. In one embodiment, the second temperature that is above the austenitic transition temperature of the martensitic alloy is preferably between about 950-1,040 degrees Celsius. In one embodiment, the proximal and distal sections of the suture needle may be locally heated using various heating methodologies including but not limited to electrical resistance heating, laser heating, induction heating, flame heating, and/or one or more combinations thereof.

In one embodiment, after locally heating the proximal and distal sections 204, 206 of the suture needle 200, the suture needle is preferably quenched to room temperature.

In one embodiment, after quenching the suture needle to room temperature, the suture needle may be tempered for increasing the ductility of the suture needle.

Figure 6:
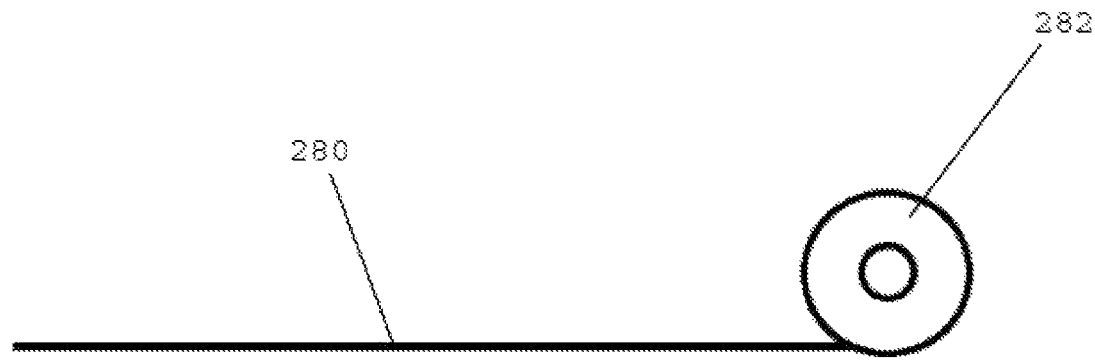
FIG. 6 shows a method of drawing a strand of wire from a wire spool, in accordance with one embodiment of the present patent application.

Referring to FIG. 6, in one embodiment, a method of making a suture needle having a bendable region preferably includes drawing a wire strand 280 from a wire spool 282. The wire strand 280 may be hardened as it is drawn from the wire spool 282. The wire strand 280, preferably made of an austenitic alloy or a martensitic-aged (mar-aged) alloy, may be used to obtain one or more needle blanks, which, in turn, may be used to make one or more suture needles having bendable regions.

In one embodiment, the wire strand 280 is preferably heated to a first temperature of between about 450-700 degrees Celsius for hardening the wire strand 280. In one embodiment, the hardened wire strand 280 may be separated (e.g., cut) into a plurality of individual needle blanks.

Figure 7:
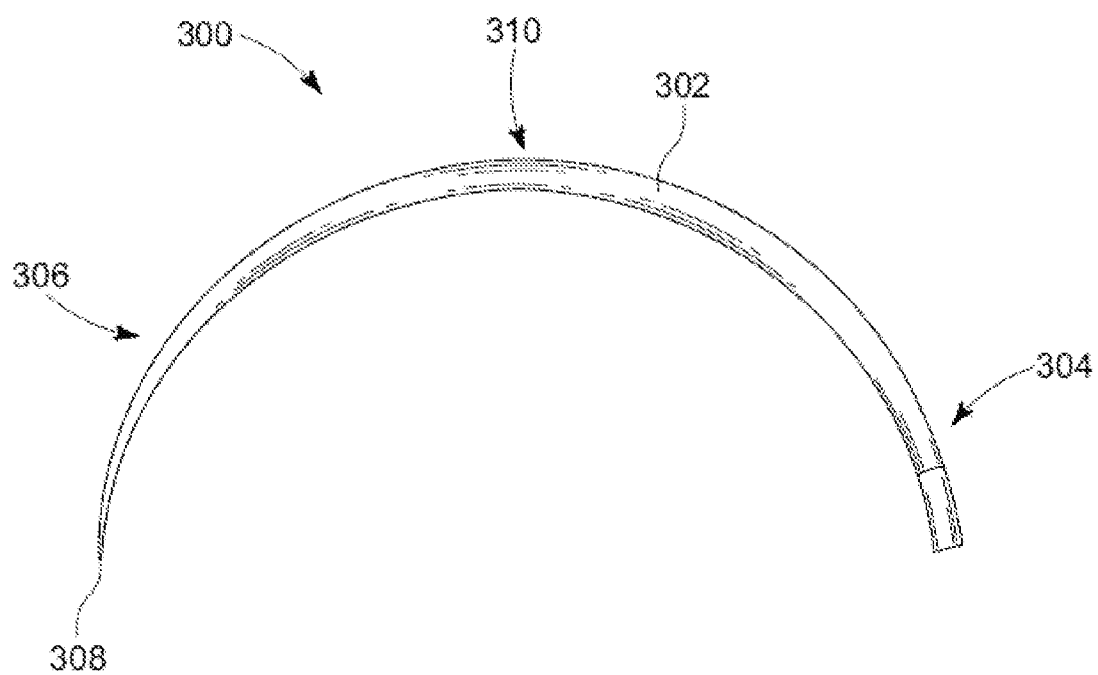
FIG. 7 shows a side view of a suture needle having a bendable region, in accordance with one embodiment of the present patent application.

Referring to FIG. 7, in one embodiment, a single needle blank may be shaped into a suture needle 300 that desirably includes an elongated body 302 having a proximal section 304, a distal section 306 with a sharpened tip 308, and a mid-section 310 that may be transformed into a bendable region by selectively heating one or more sections of the elongated body 302 of the suture needle 300 as described in more detail herein.

In one embodiment, the mid-section 310 of the elongated body 302 is preferably locally heated to a second temperature that is greater than 700 degrees Celsius, while maintaining the proximal and distal sections 304, 306 of the elongated body 302 of the suture needle 300 at a temperature that is below 700 degrees Celsius so that the mid-section 310 of the elongated body 302 is transformed into a bendable region 310 of the suture needle 300 that is softer and more flexible than the stronger, stiffer, and harder proximal and distal sections 304, 306 of the suture needle 300.

In one embodiment, the bendable region 310 may be locally heated using various methodologies including but not limited to electrical resistance heating, laser heating, induction heating, flame heating, hot gas heating, and/or combinations thereof.

In one embodiment, the wire strand 280 (FIG. 6) is preferably a martensitic-aged (mar-aged) alloy, and the heating the wire strand to the first temperature step includes precipitation heat treating the wire strand.

The softened, bendable region 310 may be located in the middle of the suture needle 300, or may be offset from the middle of the suture needle (e.g., somewhat closer to the distal point 308 or the proximal end of the suture needle). Using a heat treatment to soften the metal or alloy and provide increased reshape ductility to the bendable region 310 may be applied in conjunction with the mechanical processes described herein (e.g., providing flat surfaces to form a thinner or reduced outer diameter wire section shown in FIGS. 1A-1C and 4A-4C).

Figure 8A:
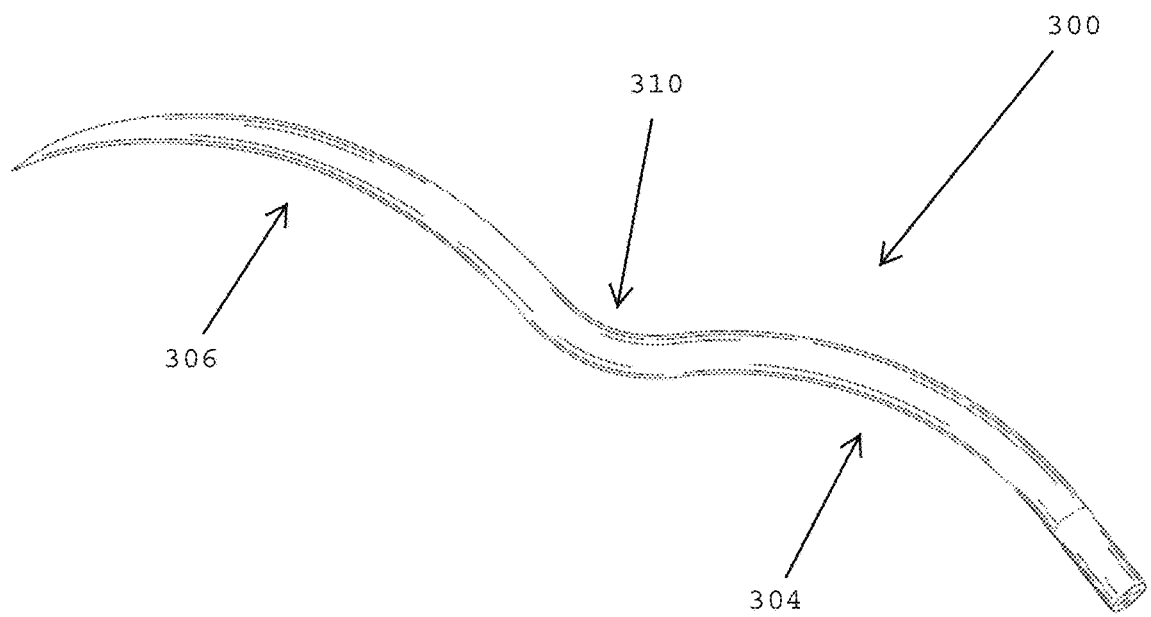
FIG. 8A shows a perspective view of the suture needle of FIG. 7 after it has been bent into a seagull shaped configuration, in accordance with one embodiment of the present patent application.
Figure 8B:
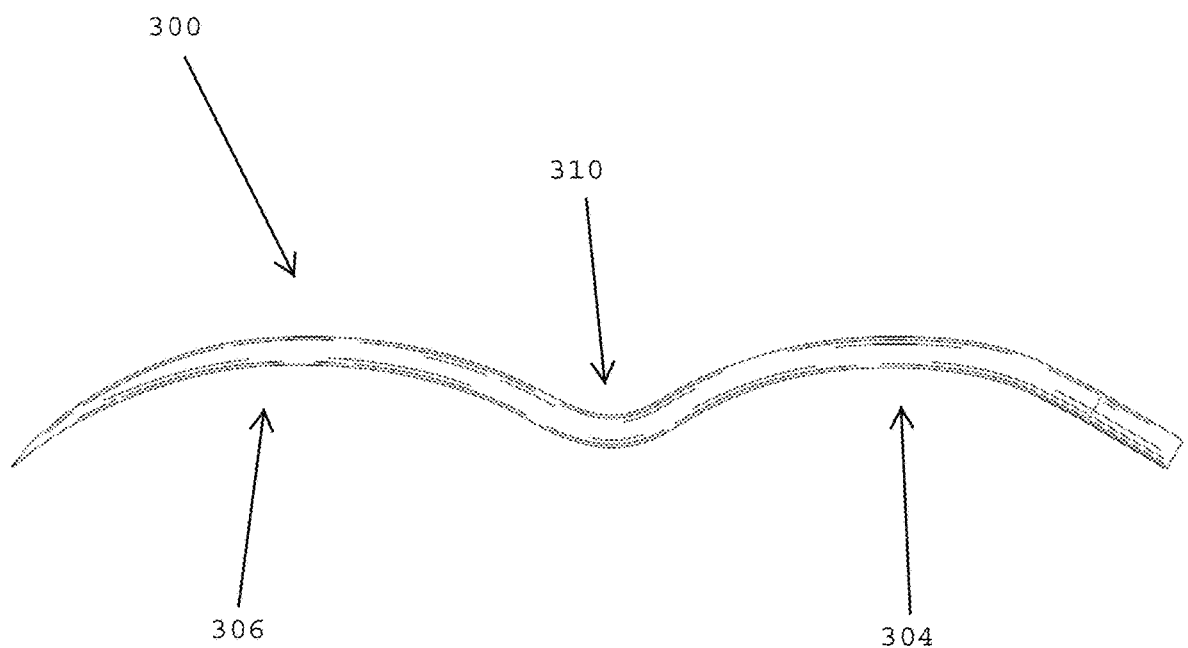
FIG. 8B shows a side view of the bent suture needle shown in FIG. 8A.

In one embodiment, the suture needle 300 shown and described above in FIG. 7 may be transformed from a semi-circular of half-circle shaped configuration to a bent configuration having a seagull shape. Referring to FIGS. 8A and 8B, in one embodiment, the suture needle 300 may be bent at the softer and/or more flexible bendable region 310 to provide the suture needle 300 with a seagull shaped configuration. In the seagull shaped configuration of FIGS. 8A and 8B, the suture needle 300 preferably has a smaller height and lower profile than the suture needle in the unbent configuration shown and described above in FIG. 7, which preferably reduces the size, height or profile of the suture needle 300 so that it may be passed through a smaller trocar (e.g., a 5 mm trocar).

In one embodiment, the bendable region 310 is preferably more flexible and less rigid than the proximal and distal sections 304, 306 of the elongated body 302 of the suture needle 300. As such, the proximal and distal sections 304, 306 of the suture needle 300 preferably maintain their respective original arc shapes as the suture needle 300 is transformed between the unbent configuration (FIG. 7) and the bent configuration (FIGS. 8A and 8B).

In one embodiment, the suture needle 300 shown in FIGS. 7 and 8A-8B may also be folded in half at the softer and more flexible bendable region 310 so that the distal tip 308 may be positioned adjacent a proximal-most end of the proximal section 304 of the suture needle 300 (e.g., see the configuration of FIGS. 5A and 5B), which also reduces the size of the needle so that it may be passed through a smaller trocar (e.g., a 5 mm trocar).

If the needle is made from an alloy that cannot exhibit substantial strengthening via a martensitic transformation, such as an austenitic stainless steel and most martensitic-aged stainless steels that exhibit relatively low amounts of carbon or nitrogen or that contain trace amounts of carbon or nitrogen, different methods should be used to produce a needle with a "bendable region". Examples of such alloys used by Ethicon include ETHALLOY®, 455, 4310 (similar to 302), and W-26% Re. ETHALLOY® and 455 are martensitic-aged alloys and may be precipitation strengthened.

Figure 9:
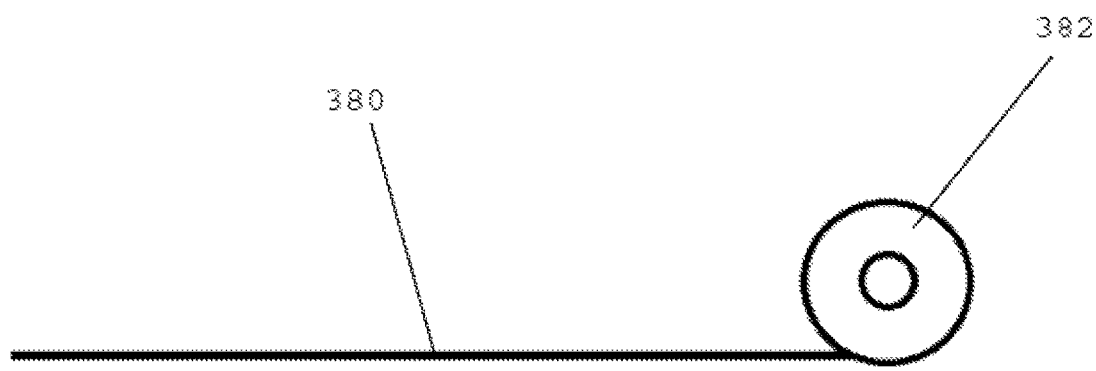
FIG. 9 shows a method of drawing a strand of wire from a wire spool, in accordance with one embodiment of the present patent application.

Referring to FIG. 9, in one embodiment, a method of making a suture needle having a bendable region preferably includes drawing a wire strand 380 from a wire spool 382. The wire strand 380 may be hardened as it is drawn from the wire spool 382. The wire strand 380, preferably made of a martensitic-aged (mar-aged) alloy, may be used to obtain one or more needle blanks, which, in turn, may be used to make one or more suture needles having bendable regions.

Figure 10:
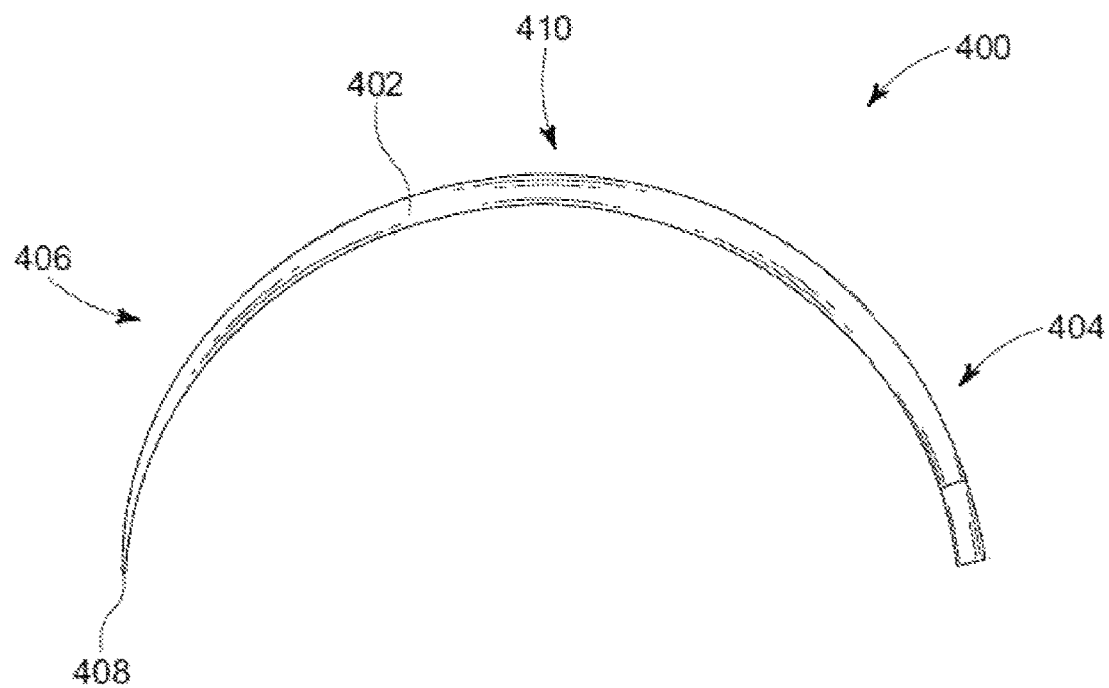
FIG. 10 shows a side view of a suture needle having a bendable region, in accordance with one embodiment of the present patent application.

In one embodiment, the hardened wire strand 380 may be separated (e.g., cut) into a plurality of individual needle blanks. Referring to FIG. 10, in one embodiment, a single needle blank may be shaped into a suture needle 400 including an elongated body 402 having a proximal section 404, a distal section 406 with a sharpened tip 408, and a mid-section 410 that may be transformed into a bendable region of the suture needle by selectively heating one or more sections of the elongated body 402 of the suture needle 400 as will be described in more detail herein.

In one embodiment, the mid-section 410 may be transformed into a bendable region of the suture needle by heat treating the martensitic-aged alloy. In one embodiment, the mid-section 410 is preferably locally heated to a first temperature that is greater than 700 degrees Celsius while maintaining the proximal and distal sections of the suture needle at a temperature that is below 700 degrees Celsius so that the mid-section 410 of the elongated body 402 transforms into a bendable region of the suture needle 400 that is softer and more flexible than the proximal and distal sections of the suture needle.

In one embodiment, after locally heating the bendable region 410 to greater than 700 degrees Celsius, the suture needle may be cooled to room temperature.

In one embodiment, after cooling the suture needle 400 to room temperature, the proximal and distal sections 404, 406 of the suture needle 400 may be heated to a second temperature of about 450-700 degrees Celsius while maintaining the bendable region 410 of the suture needle 400 at a temperature that is below the second temperature.

In one embodiment, the martensitic-aged alloy may be 455SS or a stainless steel sold under the trademark ETHALLOY having a composition of about 73% iron, 12% chrome, 10% nickel 10%, 3% molybdenum 3%, and 2% titanium.

In one embodiment, the bendable region of the suture needle may be locally heated using various heating methodologies including but not limited to electrical resistance heating, laser heating, induction heating, flame heating, hot gas heating, and/or combinations thereof.

In one embodiment, the bendable region of the suture needle may be covered and/or clamped with a heat sink while heating the proximal and distal sections of the suture needle to the second temperature of about 450-700 degrees Celsius for maintaining the bendable region of the suture needle below the second temperature.

Figure 11A:
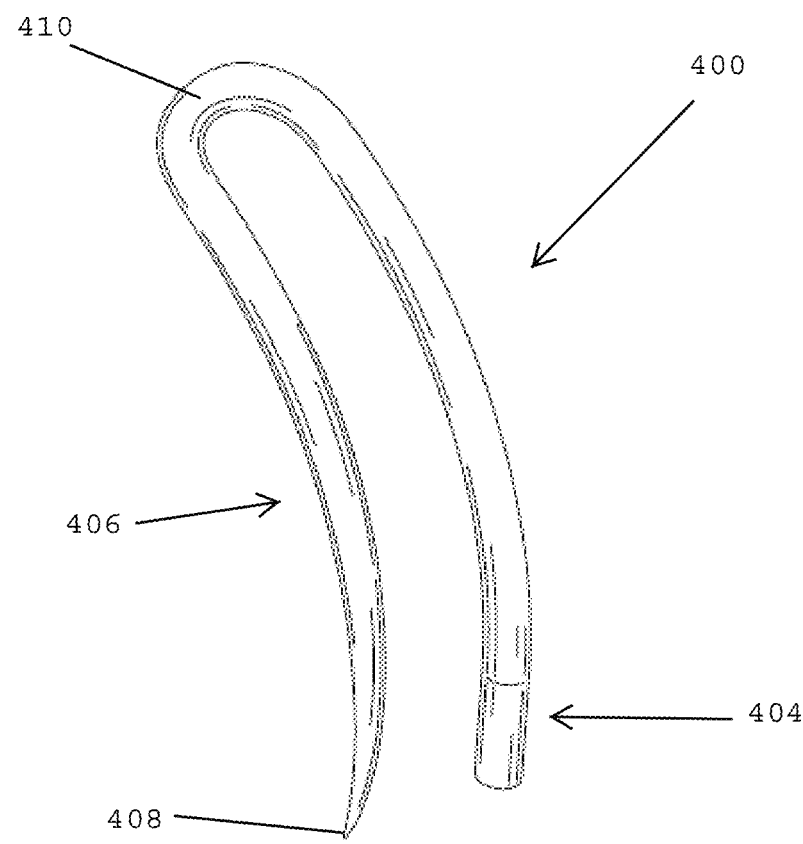
FIG. 11A shows a perspective view of the suture needle of FIG. 10 after it has been folded in half, in accordance with one embodiment of the present patent application.
Figure 11B:
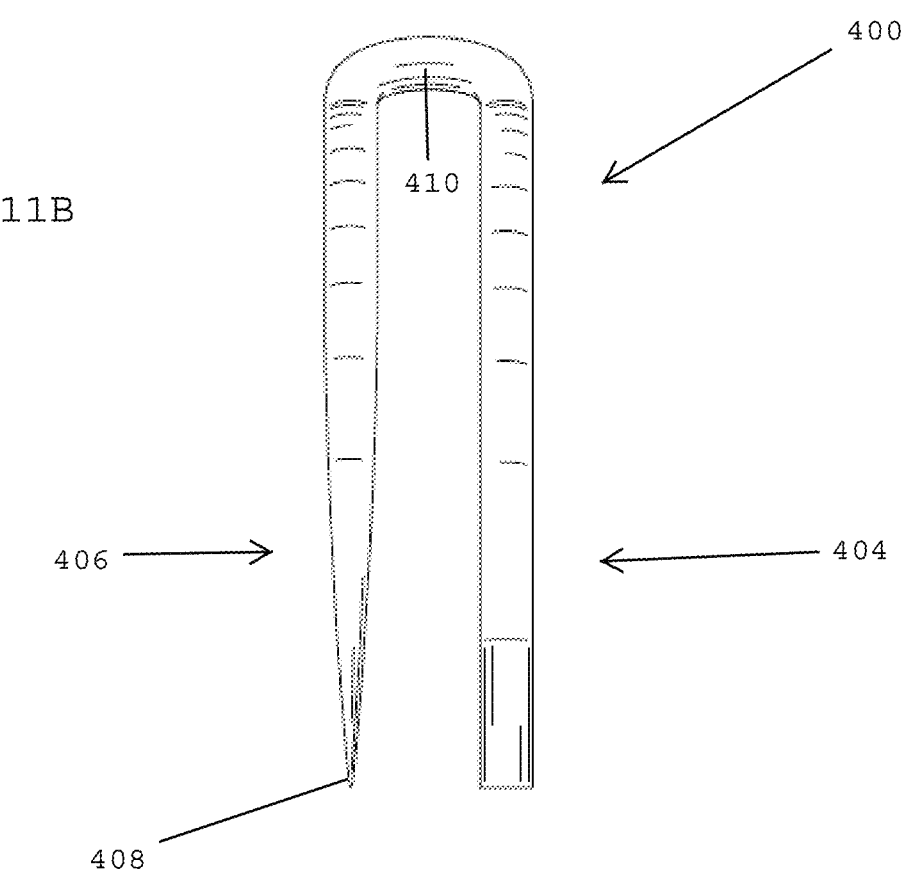
FIG. 11B shows a side view of the folded in half suture needle shown in FIG. 11A.

In one embodiment, the suture needle 400 shown and described above in FIG. 10 may be transformed from a semi-circular of half-circle shaped configuration to a bent configuration having a folded shape. Referring to FIGS. 11A and 11B, in one embodiment, the suture needle 400 may be folded in half at the softer and/or more flexible bendable region 410 to provide the suture needle 400 with a folded configuration in which the distal tip 408 may be positioned adjacent a proximal-most end of the proximal section 404 of the suture needle 400. In the folded configuration of FIGS. 10A and 10B, the suture needle 400 preferably has a smaller height and lower profile than the suture needle in the unfolded configuration shown and described above in FIG. 10, which preferably reduces the size, height or profile of the suture needle 400 so that it may be passed through a smaller trocar (e.g., a 5 mm trocar).

In one embodiment, the bendable region 410 is preferably more flexible and less rigid than the proximal and distal sections 404, 406 of the elongated body 402 of the suture needle 400. As such, the proximal and distal sections 404, 406 of the suture needle 400 preferably maintain their respective original arc shapes as the suture needle 400 is transformed between the unfolded configuration (FIG. 10) and the folded configuration (FIGS. 11A and 11B).

In one embodiment, the suture needle 400 shown in FIGS. 10 and 11A-11B may also be bent at the softer and more flexible bendable region 410 so that the elongated body 402 has a seagull shaped configuration (e.g., see the configuration of FIGS. 8A and 8B), which also reduces the size of the suture needle so that it may be passed through a smaller trocar (e.g., a 5 mm trocar).

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A method of making a suture needle having a bendable region comprising:
   obtaining a suture needle made of a martensitic stainless steel alloy having an austenitic transition temperature, said suture needle having a proximal section, a distal section with a sharpened tip, and a bendable region located between said proximal and distal sections;
   heating said suture needle to a first temperature that is greater than the austenitic transition temperature of said martensitic stainless steel alloy and quenching said suture needle to room temperature to harden said martensitic stainless steel alloy;
   after the heating and quenching steps to harden said martensitic stainless steel alloy, locally heating said bendable region of said suture needle to a second temperature that is above 800 degrees Celsius but below the austenitic transition temperature of said martensitic stainless steel alloy so that said bendable region is softened and made more flexible relative to said proximal and distal sections of said suture needle, wherein after the step of locally heating said bendable region of said suture needle to the second temperature that is above 800 degrees Celsius said proximal and distal sections of said suture needle are relatively more rigid and less flexible than said bendable region of said suture needle, wherein the first temperature that is above the austenitic transition temperature is between 950-1,040 degrees Celsius..

2. The method as claimed in claim 1, further comprising forming said suture needle into a seagull shaped configuration in which said proximal section of said suture needle defines a proximal arc, said distal section of said suture needle defines a distal arc, and said bendable region of said elongated body defines a V-shaped section that interconnects inner ends of said proximal and distal arcs, wherein said proximal arc, said distal arc, and said V-shaped section lie in a common plane.

3. The method as claimed in claim 1, further comprising forming said suture needle into a folded configuration in which said proximal section of said suture needle lies in a first plane, said distal section of said suture needle lies in a second plane that is different than the first plane, said bendable region of said suture needle interconnects inner ends of said proximal and distal sections of said suture needle, and said sharpened tip of said distal section of said suture needle is adjacent a proximal-most end of said proximal section of said suture needle.

4. The method as claimed in claim 1, wherein the second perature for locally heating said bendable region is between 800-920 degrees Celsius.

5. The method as claimed in claim 1, wherein the quenching step comprises using a gas or a liquid for cooling said suture needle.

6. The method as claimed in claim 1, wherein the locally heating step is selected from the group of heating methodologies consisting of electrical resistance heating, laser heating, induction heating, flame heating, and hot gas heating.

7. The method as claimed in claim 1, further comprising tempering said suture needle.

8. The method as claimed in claim 1, wherein the obtaining step comprises curving at least one of said proximal and distal sections of said suture needle.

9. The method as claimed in claim 1, wherein said proximal and distal sections of said suture needle body define a first outer wire diameter and said bendable region of said suture needle defines a second outer wire diameter that is smaller than the first outer wire diameter of said respective proximal and distal sections, wherein the smaller second outer wire diameter corresponds to the location of said bendable region of said suture needle that is locally heated for softening said bendable region.

10. The method as claimed in claim 1, wherein said bendable region of said suture needle comprises one or more flat surfaces, and wherein said bendable region of said suture needle is thinner than said proximal and distal sections of said suture needle, wherein said one or more flat surfaces corresponds to the location of said bendable region of said suture needle that is locally heated for softening said bendable region.

11. The method as claimed in claim 1, wherein the obtaining a suture needle step comprises:
drawing a wire strand from a wire spool;
cutting said drawn wire strand into a plurality of individual needle blanks;
shaping one of said individual needle blanks into said suture needle having said proximal section, said distal section with said sharpened tip, and said bendable region located between said proximal and distal sections, wherein the drawing, cutting and shaping steps occur prior to the locally heating said bendable region of said suture needle step.

12. The method as claimed in claim 1, wherein the obtaining a suture needle comprises:
drawing a wire strand from a wire spool, said wire strand comprising a martensitic stainless steel alloy having an austenitic transition temperature;
cutting said wire strand to provide one or more needle blanks; and
shaping one of said needle blanks into a suture needle having an elongated body including a proximal section, a distal section with a sharpened tip, and a bendable region located between said proximal and distal sections.

13. The method as claimed in claim 3, wherein the forming step comprises folding said suture needle in half from an unfolded configuration defining a semi-circular shape having a greater height to the folded configuration having a smaller height.

14. The method as claimed in claim 3, wherein in the folded configuration said first plane of said proximal section and said second plane of said distal section are parallel to one another, and wherein said proximal and distal sections of said suture needle define respective arc shapes as said suture needle is folded between an unfolded configuration having a semi-circular shape and the folded configuration.

15. The method as claimed in claim 5, wherein the step of using a gas or a liquid for cooling said suture needle comprises rapidly cooling said suture needle at a cooling rate that is greater than 100 degrees Celsius per minute.

16. The method as claimed in claim 6, wherein the tempering step comprises heating said suture needle to a temperature of 150-430 degrees Celsius for increasing ductility of said suture needle.

\* \* \* \* \*